United States Patent [19]

Rayman

[11] Patent Number: 5,529,568
[45] Date of Patent: Jun. 25, 1996

[54] MAGNETIC OPERATING TABLE

[75] Inventor: Reiza Rayman, London, Canada

[73] Assignee: Surgery Futures Research, Inc., London, Canada

[21] Appl. No.: 210,576

[22] Filed: Mar. 18, 1994

[51] Int. Cl.⁶ .................................................. A61B 17/52
[52] U.S. Cl. ............................ 600/9; 600/14; 607/57
[58] Field of Search ........................ 5/600, 607–614; 600/9–14; 607/57, 100, 103; 335/297, 298

[56] References Cited

U.S. PATENT DOCUMENTS

| | | |
|---|---|---|
| 1,149,971 | 8/1915 | Wagoner . |
| 2,671,451 | 3/1954 | Bolger . |
| 2,863,458 | 12/1958 | Modny et al. . |
| 3,043,309 | 7/1962 | McCarthy . |
| 3,474,777 | 10/1969 | Figge et al. . |
| 3,794,041 | 12/1974 | Frei et al . |
| 4,364,377 | 12/1982 | Smith . |
| 4,428,366 | 1/1984 | Findl et al. ........................ 600/14 |
| 5,163,957 | 11/1992 | Sade et al. ........................ 607/57 |
| 5,230,112 | 7/1993 | Harrawood et al. ................. 5/607 |

Primary Examiner—Angela D. Sykes
Assistant Examiner—Stephen Huang
Attorney, Agent, or Firm—Robert W. Becker & Associates

[57] ABSTRACT

A novel operating table system is provided herein. The operating table system includes a table formed of non-magnetic material. A support is provided for such table. Magnetic means are provided for applying a magnetic field around a defined area of the table. The magnetic means includes one pole below the table and a second pole disposed a selected spaced-distance above the table. The second pole includes controls for selectively focusing and translating the electromagnetic field by way of manipulation of the second pole.

12 Claims, 4 Drawing Sheets

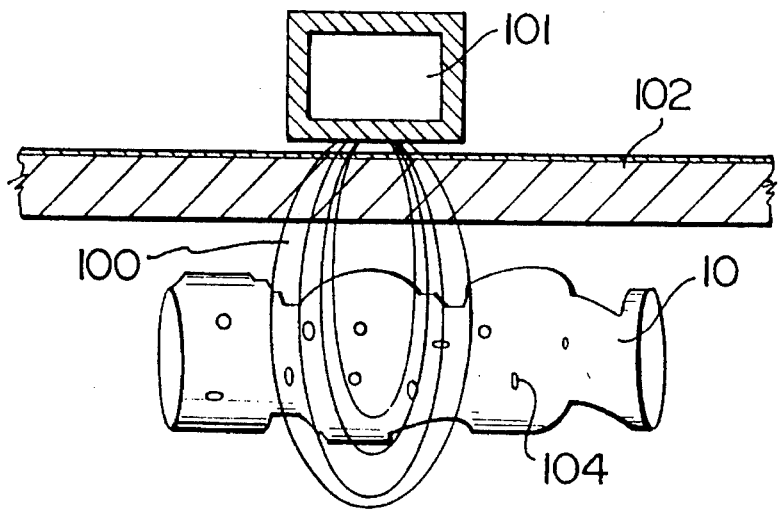
FIG.1
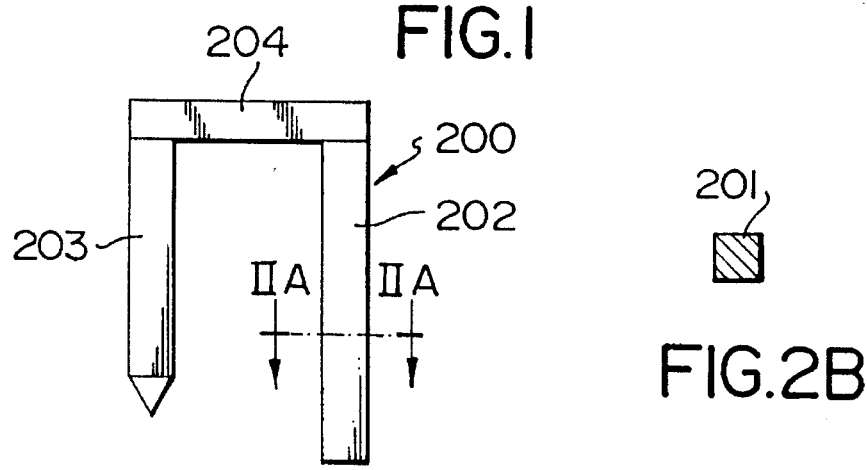
FIG.2A
FIG.2B
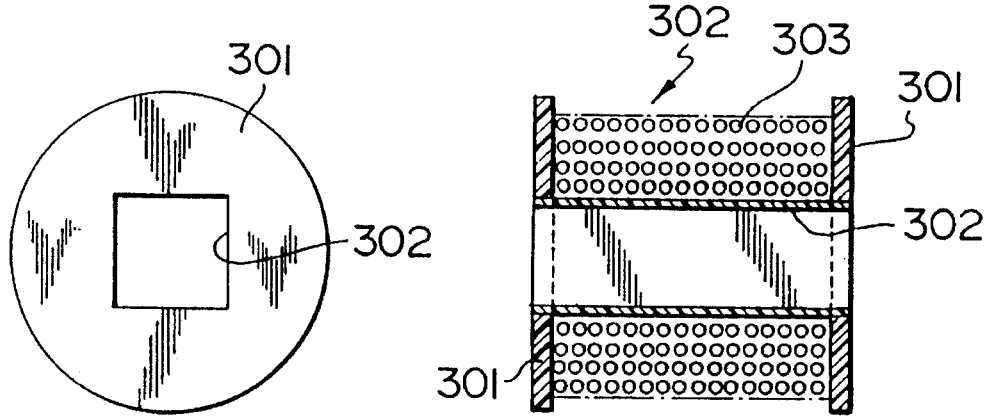
FIG.3A
FIG.3B $\Delta = T_{on2} - T_{on1} = T_{on3} - T_{on2} \cdots$

MAGNETIC OPERATING TABLE

BACKGROUND OF THE INVENTION (i) Field of the Invention

This invention relates to a magnetic, e.g., electromagnetic, operating table especially useful for laparoscopic surgery, and to a method of performing laparoscopic surgery using such operating table. It also includes novel ingestible materials for facilitating such electromagnetic laparoscopic surgery.

(ii) Description of the Prior Art

A most basic concept of surgery is one in which energy is imparted to tissues within the body. Of course, this energy is directed in exact ways to achieve a desired effect for that particular procedure.

Surgery continues to develop based partially on science, but is significantly anchored by tradition. Traditionally, surgery has been performed by the use of mechanical energy to manipulate tissue. Any clamping, grasping, cutting, or tying of tissues is effectively mechanical energy applied to that tissue. However, entire spectrums of energy remain unused and unexplored.

Energy spectrums available for consideration in surgery include tissue manipulation by the following means: mechanical (most widely used); electrical/heat (e.G., Electrocautery); pressure (e.G., Insufflation; suction); light (unused); radio (unused); magnetic/electromagnetic (unused); sound (unused); kinetic (unused); and chemical/molecular (unused).

Laparoscopic surgery is slowly changing the way surgery in the abdomen is done. Instead of large incisions, multiple thin, long-handled instruments and one long camera scope are placed through very small (2–3 mm) incisions. Surgery is done using the television view (provided by the camera scope) in conjunction with the long-handled instruments that extend from the surgical site, outside the body, and to the surgeon's hand. Such mini incisions greatly decrease surgical complications and post surgical recovery periods. In this type of surgery, manipulation is performed by means of thin instruments extending from within the body to outside the body, thus eliminating the need for full abdominal incisions. A long camera scope is used to visualize surgical manipulations within the body.

Currently, the intestine is adjusted laparoscopically using long gripping instruments. This method is quite tedious and time consuming. It would therefore be an improvement if the intestine could be adjusted by the use of magnetic means following the ingestion of magnetic or magnetizable materials.

The concept of the use by ingestion or otherwise of magnetic or magnetizable materials in medical and/or surgical techniques is known. For example U.S. Pat. No. 2,671,451 patented Mar. 9, 1959 by S. J. Bolger, titled "Remedial Pill", provided a remedial pill comprising a remedial substance which was soluble in the human body and a magnetically attractable metallic element associated with the substance. In use, a magnet was applied to the exterior of the body and the remedial pill was ingested. The pill travelled to the area of the magnet, where it was attracted and held. The remedial substances then dissolved. This patent is not concerned with manipulation of the intestines, e.g., retraction suspension or longitudinal translation of intestine segments to ease the performance of laparoscopic surgery. On the other hand, this patent is merely directed to the treatment of localized disorders of the alimentary canal, particularly ulcers where it was very difficult to apply a remedy to the affected spot for the reason that there was a constant flow through the canal caused by the normal digestive processes.

U.S. Pat. No. 3,043,309 patented Jul. 10, 1962 by H. F. McCarthy, titled "Method of Performing Intestinal Intubation", provided a method and means for performing intestinal intubation. The method involved securing a magnetic member to the tip of an elongated, X-ray opaque, flexible tube. The tip and tube were then passed through the oesophagus to the stomach of a patient. The stomach region was then illuminated by means of X-rays, and the tube was observed on a fluoroscopic screen. A maneuverable magnetic field was then applied to the magnetic material to direct the tip, to which the magnetic material was secured, to the pylorus valve in the stomach. A highly flexible intubation tube was adapted to pass through the intestinal tract of a patient. A magnet was positioned in the tip of the intubation tube. An electromagnet was provided for generating a magnetic field which coupled the magnet in the intubation tube and developed an attractive or repulsive force on the magnet, whereby the intubation tube could be directed in a predetermined direction. However, this patent is not directed to manipulation of the intestines, e.g., retraction suspension or longitudinal translation of intestine segments to ease the performance of laparoscopic surgery. This patent is merely directed to intestinal intubation, including an electromagnetic means which made it suitable for manual manipulation during an intubation operation.

U.S. Pat. No. 3,474,777 patented Oct. 28, 1969 by F. H. J. Figge et al, titled "Method of Administering Therapeutic Agents" provided a method of localizing a therapeutic agent at a preferred treatment site within an organism by injecting the agent into the organism in association with a magnetically-responsive substance. The agent and substance were concentrated at the preferred treatment site by the application of magnetic fields to the organism. Microcapsules and/or particles adaptable to injection and having a maximum size of five microns included a therapeutic agent in association with a magnetically responsive substance. The patent taught that the magnetically responsive substance may be coated with, or dispersed within, a therapeutic agent or, conversely, that a magnetically-responsive substance may be used to coat or partially coat a therapeutic agent, or as a matrix for the agent. When the particles were employed in the form of microcapsules, the magnetically-responsive substance could be within the capsule shell, or the magnetic substance could form part of a shell encapsulating a therapeutic agent. However, this patent is not directed to manipulation of the intestines, e.g., retraction suspension or longitudinal translation of intestine segments to ease the performance of laparoscopic surgery. On the other hand, this patent is only concerned with the provision of means for localizing therapeutic agents within the organism at those sites specifically desired to be treated with the therapeutic agent, without being dispersed generally throughout the organism.

U.S. Pat. No. 3,794,041 patented Feb. 26, 1974 by E. H. Frei et al, titled "Gastrointestinal Catheter" provided a gastrointestinal catheter of elongated flexible shape, including ferromagnetic material. When the catheter was inserted into the cavity of a body part, it would be attracted by a magnet external of the body in order to manipulate the body part with the catheter. The ferromagnetic material included a plurality of ellipsoidal beads of soft iron in the catheter in closely adjacent spaced relationship therein over a substantial length thereof. The soft iron ellipsoidal beads were fixed in the relationship by the resiliency of the flexible tubular members. The patentee further taught the provision of a coating of plastic, e.g., polyethylene, of adequate thickness, on the iron beads. In use, the gastrointestinal catheter was adapted, when inserted into the cavity of a body part, to be uniformly and unidirectionally attracted by a magnet external of the body for desired displacement of the body part substantially without the application of torque to the beads. However, this patent is not directed to manipulation of the intestines, e.g., retraction suspension or longitudinal translation of intestine segments to ease the performance of laparoscopic surgery. On the other hand, this patent is only concerned with a solution to the problem that, in certain types of disease, the only effective treatment consists of massive irradiation of the afflicted organ by concentrating the treatment at that organ.

U.S. Pat. No. 4,364,377 patented Dec. 21, 1987 by F. W. Smith, titled "Magnetic Field Hemostasis" taught a method for staunching blood flow from a bleeding gastrointestinal lesion. The method included introducing, into the gastrointestinal tract, a suitable tamponading mass having ferromagnetic properties. One such suitable tamponading mass was a mixture of finely divided iron particles and vegetable oil which may be introduced through an endoscopic catheter. Once in the gastrointestinal tract, the tamponading mass was moved as necessary to cover and press upon the bleeding lesion by a magnetic field generated outside the body, e.g., by an electromagnet. The positioning was under the direct visual control of the endoscopist. However, this patent is not directed to manipulation of the intestines, e.g., retraction suspension or longitudinal translation of intestine segments to ease the performance of laparoscopic surgery. On the other hand, this patent is only concerned with the difficulties of stopping the bleeding of gastrointestinal lesions such as acutely bleeding ulcers.

SUMMARY OF THE INVENTION (i) Aims of the Invention

Thus, none of the above prior art is directed to laparoscopic surgery techniques. In particular none of the prior patents is directed to the essence of the present invention, namely the manipulation of the intestines, e.g., retraction, suspension or longitudinal translation of intestine segments to ease the performance of laparoscopic surgery.

Accordingly, the present invention has for its main object the provision of a device, and apparatus of a magnetic nature, for manipulating intestine segments during laparoscopic surgery.

Another object of the present invention is the provision of an operating table, associated with magnetic means, for manipulating intestine segments during laparoscopic surgery.

Yet another object of the present invention is the provision of a method of a magnetic nature for manipulating intestine segments during laparoscopic surgery.

(ii) Statements of Invention

This invention provides an operating table system comprising a table formed of non-magnetic material, a base support for the table; a generally-rectangular framework secured to the base support, the framework including a front column, a lower base member, a rear column, a forwardly-cantilevered plate and a depending downward leg; and a translation movement electromagnet for applying a magnetic field around a defined area of the table, the translation movement electromagnet including a lower pole connected to the base support below the table, and an upper pole, the upper pole being secured to the depending downward leg and disposed a selected spaced-distance above the table, the upper pole including means for selectively focusing and translating the electromagnetic field by way of manipulation of the upper pole.

This invention also provides a method for manipulating intestine segments during laparoscopic surgery of a patient. The method includes the steps of: pre-operatively providing a magnetic or magnetizable zone within a segment of the intestine, e.g., by having the patient ingest a viscous medium including a set of plastic-coated particles of magnetic or magnetizable material, or by having the patient ingest a ferromagnetic fluid which becomes gel-like in the presence of a magnetic field; applying a magnetic field around the patient by poles spaced above and below the patient to attract the intestine segments having the magnetic or magnetizable zone therein to the magnetic field; and varying the strength and orientations of the magnetic field during the laparoscopic surgery to manipulate the intestine.

This invention still further provides an ingestible fluid including a viscous medium containing a plurality of plastic-coated, magnetic or magnetizable pills, for ingestion by a patient for accumulation in the intestines for manipulating the intestines during laparoscopic surgery.

(iii) Other Features of the Invention

By one feature of the operating table system of this invention, the magnetic means comprises an electromagnet including a magnetic core, a coil surrounding one portion of the core, the coil being adapted to be supplied with DC current, a pole head disposed a selected, spaced-distance above the table, and a magnetic pole plate below the table.

By another feature thereof, joints between the lower base member and the rear column, and between the forwardly cantilevered plate and the depending downward leg are flexible.

By another feature thereof, the upper pole includes a plurality of expandable pole heads supported on a rotatable shaft magnet.

By yet another feature thereof, the upper pole includes a plurality of rotatable magnetic poles disposed in a cog wheel fashion.

By still another feature thereof, the upper pole includes a plurality of rotatable magnetic poles disposed in a cog wheel fashion.

By a still further feature thereof, the upper pole includes a magnetizable helical shaft and means to rotate the helical shaft to effect a change in the strength of the magnetic field.

By yet a further feature thereof, the upper pole includes a series of magnetically-active wire coils, and means selectively adjustable to adjust the electromagnetic field according to the individual strength of the separate magnetic coils.

By still another feature thereof, the operating table includes a mechanically-operated means for moving the pole head longitudinally with respect to the length of the operating table.

By a further feature thereof, the coil comprises a steel core, wrapped with a plurality of individual coils and encased in a synthetic plastic casing, e.g., polytetrafluoroethylene.

(iv) Generalized Description of the Invention

In more general terms, in the present invention, an electromagnetic operating table is provided in order to manipulate the intestines surgically during laparoscopic surgery, without any physical contact with them. Such table is capable of having its electromagnetic field adjusted to provide specific movement of the complete intestine length during laparoscopic surgery.

The novel electromagnetic operating table consists of a magnetically-inert patient table which is adjustable in height, tilt, and roll. Surrounding it is an electromagnetic core. The poles of the electromagnet are positioned above and below the patient's body. When the patient ingests the viscous fluid, to provide magnetic or magnetizable zones within the intestine, e.g., the viscous fluid including the magnetic pill, or the ferromagnetic fluid which becomes gel-like in the presence of a magnetic field, as previously described, and when the electromagnetic field above the patient's body is adjusted, specific manipulation of the intestines can be achieved.

The electromagnetic field may be adjusted above the patient's body by various design features of the electromagnet head. In one embodiment, the head of the electromagnet consists of rotatable magnetic poles in a cog wheel fashion. In a second embodiment, electromagnetic field adjustment is provided by movement of a helical shaft as the electromagnet head. In a third embodiment, manipulation of the magnetic field is provided via separately controlling small magnetic coils constituting the coil.

The electromagnet design of the operating table allows an intestine segment to be attracted and suspended for surgical manipulation. Then, the electromagnet field is adjusted in concert with the surgical operation to provide controlled manipulation of the intestines.

The present invention thus provides to a surgical operating table which will enable the electromagnetic manipulation of intestine segments during laparoscopic surgery. Such manipulations include the suspension or retraction of an intestine segment, or the lengthwise translation of the entire intestine in a segment-by-segment fashion (i.e., "running" the intestine).

In the practice of this invention, a magnetically-attractive viscous medium (as previously described) is ingested by the patient pre-operatively, and is distributed evenly in the intestinal tract. The electromagnetic field is introduced upon the abdomen intraoperatively and manipulation of the field thereby translates intestine lengths within the abdomen. The magnetic field may be preferably applied by an electromagnet, or by a permanent magnet.

One embodiment of the magnetic medium is one which contains magnetically-attractive (but non-magnetizing) particles within a viscous fluid. The fluid serves to prevent coalescence of particles when under the influence of the electromagnetic field. The ideal shape, size, and distribution density of the particles is empirically derived by practice. The magnetic or magnetizable material may be of soft iron with a protective coating or steel spheres, or a nickel-steel spherical shape, e.g., wherein the spheres are 2–3±0.01 mm in diameter. A spherical shape and maximal diameter of 2–3 mm is believed to be optimal. In respect of ideal particle distribution density and size, soft iron spheres of 2–3 mm diameter spaced at one per 0.5 to 1 cm² apart may be used.

Another embodiment of the magnetic medium is a commercially-available ferromagnetic fluid which becomes gel-like under the influence of a magnetic field.

The strength of the magnetic field, which is preferably produced by an electromagnet, should preferably be between 0.1 and 0.5 tesla. It may be induced by an electromagnet or by suitable movably-mounted permanent magnets. Any non-ideal distribution of magnetic particles within the intestine may be compensated by an adjustment of the magnetic or electromagnetic force.

The plastic of the plastic-coated particles is a food-grade synthetic plastic material, e.g., polyethylene, polyvinyl chloride, polypropylene, etc.

BRIEF DESCRIPTION OF THE DRAWINGS

In the accompanying drawings,

FIG. 1 is a schematic view showing the concept of electromagnetic manipulation;

FIG. 2 is a composite schematic representation of one suitable electromagnet core, where FIG. 2A is an elevational view and FIG. 2B is a cross-sectional view along the line IIA—IIA of FIG. 2A;

FIG. 3 is a schematic representation of one suitable coil, in which FIG. 3A is an end elevational view and FIG. 3B is a side elevational view;

Figure 4:
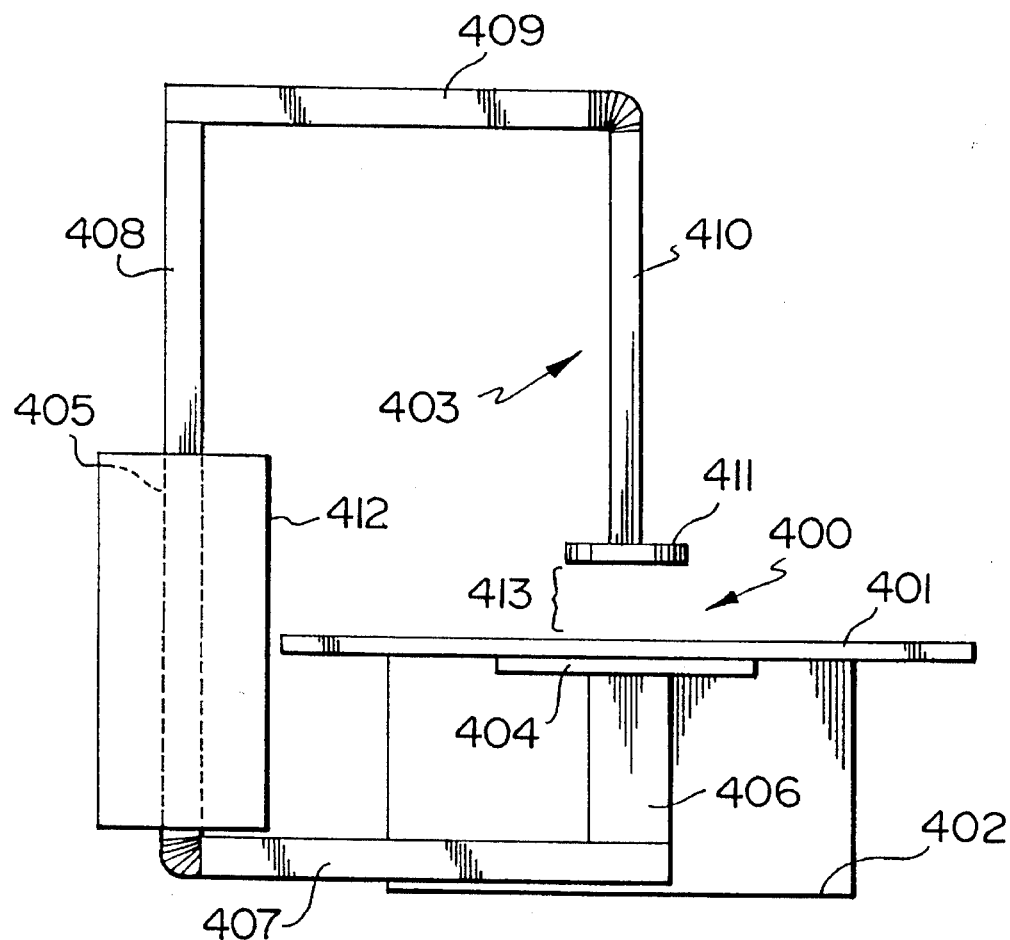
FIG. 4 is an overall side elevational view of the electromagnetic operating table.

DESCRIPTION OF PREFERRED EMBODIMENTS (i) Description of FIG. 1

As seen in FIG. 1 a magnetic field 100 is produced by an electromagnet 101, which penetrates the abdominal wall 102 and passes through the intestine segment was 103. A magnetic medium 104, e.g., plastic-coated iron pellets are of a viscous nature and are introduced pre-operatively via a nasogastric tube (not shown). The simple interaction between the magnetic power and the particle field determines the success of intestine attraction of this invention.

(ii) Description of FIGS. 2 and 3

As seen in FIGS. 2, i.e., 2A and 2B and 3, i.e., 3A and 3B, the core 200 is an inverted U-shaped framework of square solid cross-section 201 (see FIG. 2B) including a long leg 202, a shorter pointed leg 203 and an upper bridge 204.

The core 300 includes two end discs 301 provided with a square hollow core 302. A plurality of windings 303 in the core 302 provide the means of producing the electromagnetic field.

Lug 202 is adapted to be inserted through square hollow core 302.

It is known that magnetic force decays with distance away from the magnet face in approximately a cubic manner (i.e., F is inversely proportional to $X^3$ where X is distance). An increase in the number of wire turns around the electromagnet core and the shape of the core itself will increase the magnetic force produced. A U-shaped design electromagnet seems feasible. Liquid cooling of the wire coils may be required to minimize resistance, and therefore allow greater current passage and greater magnetic force.

In respect of magnetic field interference, the current steel composition of laparoscopic instruments may interfere with the electromagnetic field. It is therefore desirable to use magnetically-inert surgical instruments.

(iii) Description of FIG. 4

FIG. 4 illustrates the complete structure of the electromagnetic operating table 400. This consists of a magnetically-inert patient table 401 supported on a conventional base 402 which is adjustable in height, pitch, and roll. The electromagnet 403 includes a base pole in the form of a flat iron plate 404 situated underneath the patient table 401. The magnetic core 405 continues as a front column 406 at the mid portion of the table 401, and extends downwardly to the table base 402, thence along the floor as a base member 407 to the foot of the table, then upwardly as a rear column 408, then forwardly as a cantilevered plate 409 and finally projecting downwardly as leg 410 to extend above the patient's body where the electromagnetic head 411 is disposed. The entire magnet core structure 405 is a continuous iron element. A copper wire coiling 412 produces the magnetic field, and is situated at the foot of the table 401 surrounding the vertical rear column 408 of the core 405. In one embodiment, the iron core measures approximately 5 cm×5 cm in cross-section. The wire coiling 412 of the electromagnet requires a heat dissipation system (not shown) as well as a power system (not shown) to provide electromotive force. The DC electrical current provided to the system is adjustable so that the magnetic field in the air gap 413 between the table 401 and the electromagnet head 411 ranges from 0.1 to 0.5 T. The field strength required is that which is necessary to lift intestinal segments.

Figure 5:
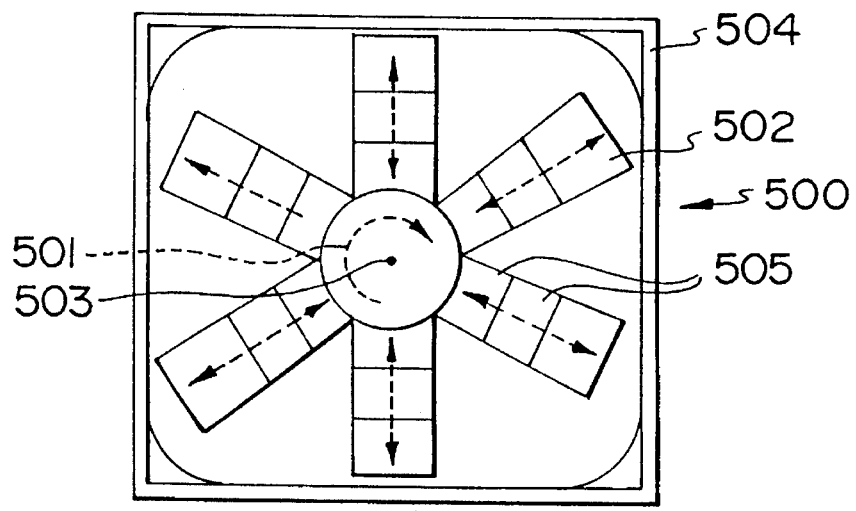
FIG. 5 is a schematic view of one embodiment of the electromagnet head which consists of rotatable poles.

(v) Description of FIG. 5

FIG. 5 illustrates one embodiment of a magnetic head 500 of the operating table 400 which consists of a plurality of stacked, rotatable shafts 501 each provided with an expandable salient pole 502. The rotatable shafts 501 are adapted to rotate about a common axis 503, and such rotation is produced by a variable speed electric motor (not shown). The entire structure is contained within a magnetically-inert rectangular box 504. Each individual pole is constructed of concentric iron cylinders 505, such that the length of a pole may be changed in a telescopic fashion. The magnetic attraction between a pole and the table base governs the pole length. As rotation of the shafts occur, longitudinal translation of the intestinal length is achieved.

Figure 6:
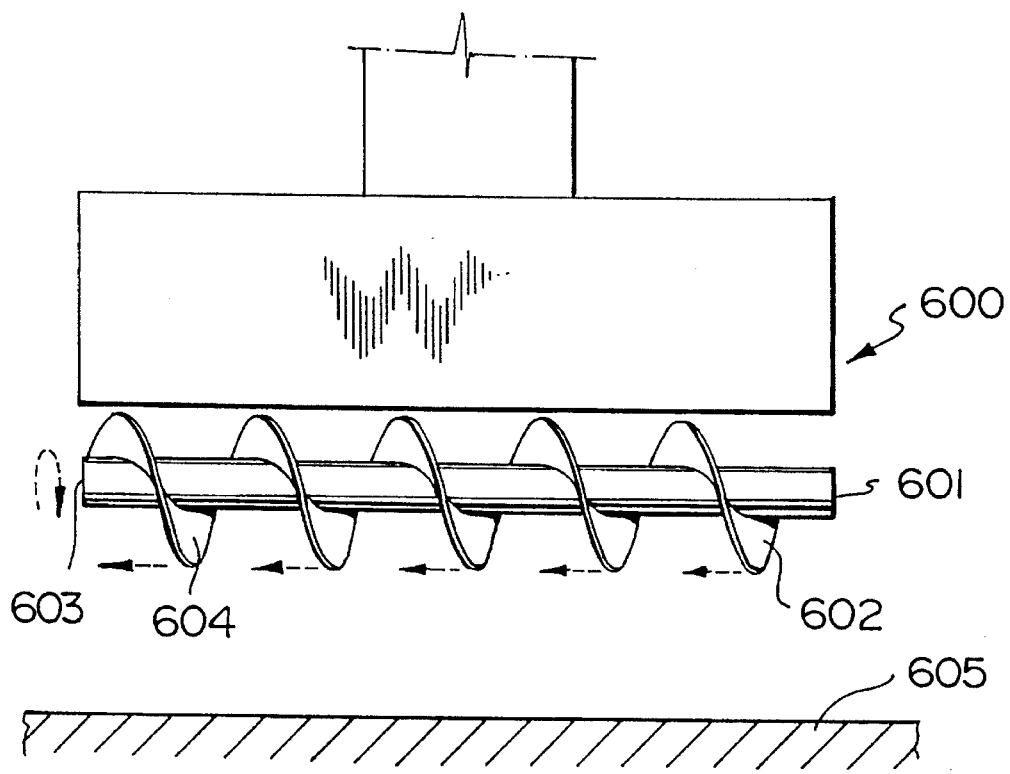
FIG. 6 is a schematic view of a second embodiment of the electromagnet head which includes a helical rotatable shaft.

(vi) Description of FIG. 6

FIG. 6 illustrates an embodiment of the operating table magnetic head 600 which is a rotatable helical shaft 601 situated above the magnetic plate 605. This embodiment of the magnetic head is used alone or in combination with other versions, depending on the surgical manipulations desired. The helical shaft 602 is adapted to rotate about its longitudinal axis 603 and is driven by a variable speed electric motor (not shown). In one embodiment, the entire structure measures approximately 20 cm in length with the helix pitch about 5 cm. Rotation of the helix 604 effects change in magnetic field strengths, and results in longitudinal translation of the intestine. Different versions of the helix could vary in pitch, again depending on the type of manipulation required.

The electromagnetic heads described with respect to FIGS. 5 or 6 are used alone or in combination during the completion of a laparoscopic surgery case. In one embodiment, an appropriate magnet head for that procedure will be selected pre-operatively, and would then be used during the entire operating procedure.

The above embodiments provide an overall description of a surgical operating table using electromagnetic fields for aiding laparoscopic surgery.

Figure 7:
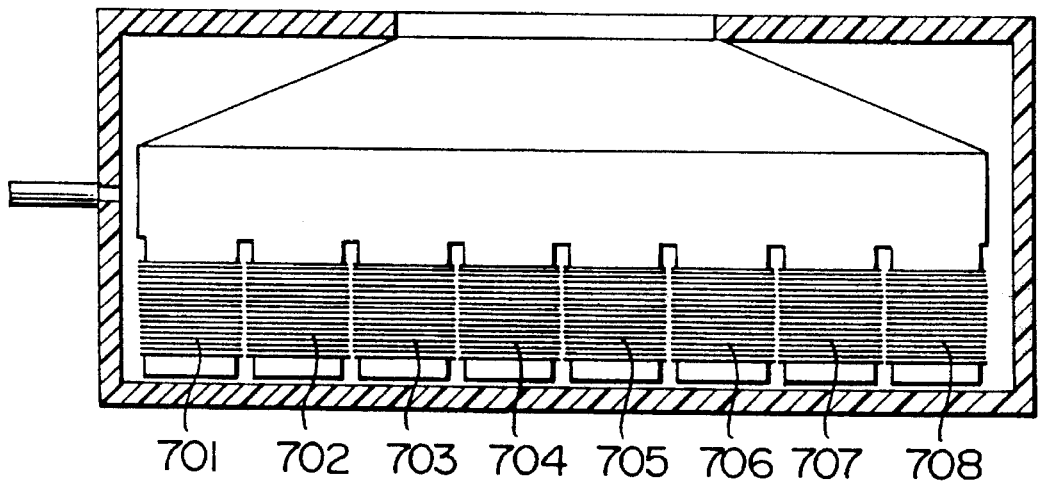
FIG. 7 is a central, longitudinal section through another embodiment of the magnetic head of this invention.

(vii) Description of FIG. 7

As seen in FIG. 7, the embodiment of the coil 700 is a series of magnetically-active wire coils 701–708 to provide a third embodiment of the magnetic head 710. The total magnetic field can be adjusted according to the individual strength of the coils 701–708.

Figure 8:
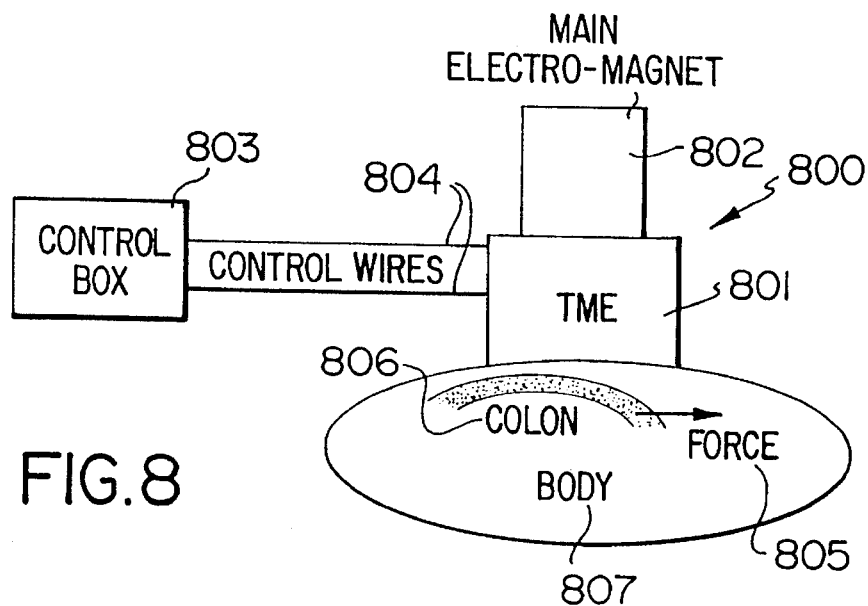
FIG. 8 is a schematic representation and overview of the operating system for the electromagnet operating table of this invention.

(viii) Description of FIG. 8

FIG. 8 shows an over view of the general system 800. The system includes a translation movement electromagnet (TME) 801, as previously described, which includes a main electromagnet 802, and a control box 803 connected thereto by control wires 804.

The TME attaches to the main electromagnet via a low reluctance connection. The individual coils 701–708 are exited by current waveforms produced by the circuitry associated with the control box.

Figure 9:
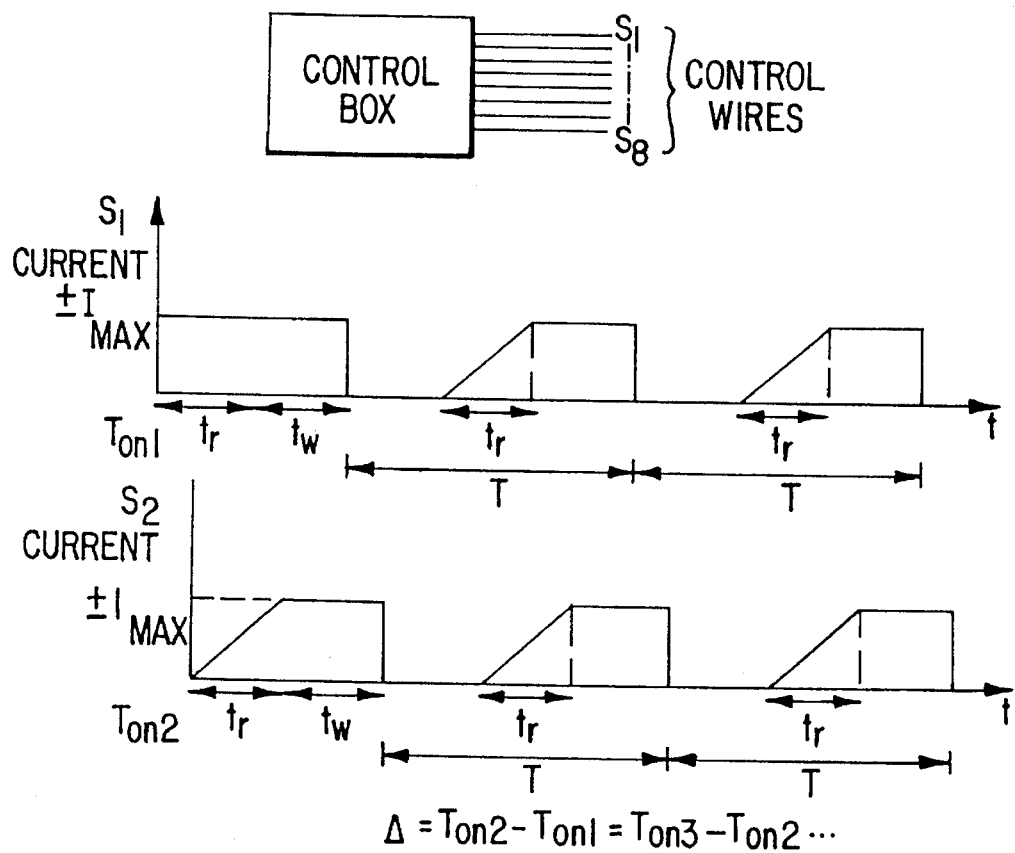
FIG. 9 is a schematic representation of the control box and associated current waveforms.

(ix) Description of FIG. 9

The control box outputs the current waveforms shown in FIG. 9. The rise time, $t_r$, pulse width, $t_w$, and period, T, can be varied via control knobs. The phase relationship between the waveforms of each individual coil, d, can also be varied via a control knob. The polarity of each wave form can be positive or negative in order to increase the gradient of the produced magnetic field.

Generalized Description of the Operation of the Invention

The use of laparoscopic techniques for performing abdominal surgery is advantageous for the patient (decreased morbidity etc) but awkward for the surgeon. This is especially true in intestine surgery, because the small gripping area of laparoscopic instruments make continuous lengths of intestine difficult to manoeuvre. The development of an electromagnetic device, according to the present invention, which is adapted to grip, retract, or run intestine lengths extracorporeally thus would ease the performance of laparoscopic procedures.

The electromagnetic table allows a magnetic or magnetizable zone within a segment of the intestine, e.g., a viscous ferromagnetic particle-containing solution, or a ferromagnetic fluid which becomes gel-like in the presence of a magnetic field, which has been ingested by the patient and resides within the intestines, to be attracted to the electromagnet head. This solution is a fluid which may be a biologically-inert, semi-viscous gel (e.g., a gelatin) containing plastic-coated, stainless steel, or other ferromagnetic particles, or a ferromagnetic fluid which becomes gel-like in the presence of a magnetic field. The particles are approximately 1 mm in greatest diameter. The solution is ingested by the patient pre-operatively. Post-operatively, the natural peristaltic movement of the intestines excretes the fluid from the body, without any biologic impact to the patient. Intestinal segment replicas were used in the laboratory to identify the ideal distribution density of ferromagnetic particles. One particle per 0.5 to 1.0 $cm^2$ of surface area of the intestine provided optimal attraction to the magnetic source. Particles less than 1 mm in diameter were shown to be more highly attracted to the magnetic source than larger particles.

The magnetic operating table produces a specifically-generated and controlled magnetic field for the movement of the intestines. Any other magnetically-active elements within this field can adversely change field characteristics. Therefore, all other laparoscopic instruments used for surgical manipulations must be magnetically inert.

Simple attraction of an intestine loop to the inside of the abdominal wall is not sufficient for intestine manipulation. Retraction and translation of intestine segments (i.e., "running" the intestine) is more useful. Running intestine segments could be done using tandem electromagnets with a rotating core as previously described.

In respect of adhesions, intestine adhesions cannot be overcome by the electromagnetic force. In this case conventional laparoscopic instruments would be used until discrete adhesions are released.

Attraction of the intestines towards the magnetic source is the key to success of the operating table of this invention. Force can be increased by using high current, large amounts of wire coiling, possibly liquid cooling of wires, and U-shaped coil design.

The electromagnetic operating table described hereinabove, will ease greatly the laparoscopic manipulation of intestine lengths. Therefore, it will both speed the completion of current laparoscopic surgeries and widen the scope of procedures done laparoscopically.

In order to enable electromagnetic forces to retract, suspend, or longitudinally translate intestine segments to ease the performance of laparoscopic surgeries, it was found to be necessary to provide the magnetic field coil surrounding the patient to attract the biologically-inert ferromagnetic fluid in the biologically-inert, ferrous particles which have been ingested by the patient pre-operatively.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. An operating table system comprising:

a) a table formed of non-magnetic material;

b) a base support for said table;

c) a generally-rectangular framework secured to said base support said generally-rectangular framework including a front column, a lower base member, a rear column, a forwardly-cantilevered plate and a depending downward leg; and d) a translation movement electromagnet for applying an electromagnetic field around a defined area of said table, said translation movement electromagnet including a lower pole connected to said base support below said table, and an upper pole, said upper pole being secured to said depending downward leg and disposed a selected spaced-distance above said table, said upper pole including means for selectively focusing and translating said electromagnetic field by way of manipulation of said upper pole.

2. The operating table system of claim 1, wherein said electromagnet includes a magnetic core surrounding a portion of said rear column and a coil surrounding one portion of said core, said coil being adapted to be supplied with DC current.

3. The operating table system of claim 1, wherein joints between said lower base member and said rear column, and between said forwardly-cantilevered plate and said depending downward leg are flexible.

4. The operating table system of claim 1, wherein said upper pole includes a plurality of expandable pole heads supported on a rotatable shaft magnet.

5. The operating table system of claim 4 wherein said upper pole includes a plurality of rotatable magnetic poles disposed in a cog wheel fashion.

6. The operating table of claim 2 wherein said coil comprises a steel core, wrapped with a plurality of individual coils and encased in a synthetic plastic casing.

7. The operating table of claim 6 wherein said synthetic plastic casing is polytetrafluoroethylene.

8. The operating table of claim 6 including means selectively engageable to adjust the electromagnetic field.

9. The operating table of claim 1 including means selectively engageable to adjust the table in height, tilt and roll.

10. The operating table system of claim 1, wherein said upper pole includes a plurality of rotatable magnetic poles disposed in a cog wheel fashion.

11. The operating table system of claim 1 wherein said upper pole includes a magnetizable helical shaft and means to rotate said helical shaft to effect a change in the electromagnetic field strength.

12. The operating table system of claim 1, wherein said upper pole includes a series of magnetically-active wire coils, and means selectively adjustable to adjust the electromagnetic field according to individual strength of the separate magnetic coils.

\* \* \* \* \*